(12) United States Patent
Hong et al.

(10) Patent No.: US 12,102,669 B2
(45) Date of Patent: Oct. 1, 2024

(54) COMPOSITIONS FOR INHIBITING TERATOMA FORMATION AND GROWTH COMPRISING TIMP-1 AND TIMP-2 AS EFFECTIVE COMPONENTS

(71) Applicant: Korea University Research and Business Foundation, Seoul (KR)

(72) Inventors: Sung Hoi Hong, Seoul (KR); Kyung-Ah Choi, Cheorwon-gun (KR)

(73) Assignee: Korea University Research and Business Foundation, Seoul (KR)

( * ) Notice: Subject to any disclaimer, the term of this patent is extended or adjusted under 35 U.S.C. 154(b) by 796 days.

(21) Appl. No.: 17/274,657

(22) PCT Filed: Jul. 18, 2019

(86) PCT No.: PCT/KR2019/008896
§ 371 (c)(1),
(2) Date: Mar. 9, 2021

(87) PCT Pub. No.: WO2020/054962
PCT Pub. Date: Mar. 19, 2020

(65) Prior Publication Data
US 2022/0031819 A1 Feb. 3, 2022

(30) Foreign Application Priority Data

Sep. 10, 2018 (KR) .................. 10-2018-0107637

(51) Int. Cl.
*A61K 38/57* (2006.01)
*A61K 35/30* (2015.01)
*A61K 35/545* (2015.01)

(52) U.S. Cl.
CPC .............. *A61K 38/57* (2013.01); *A61K 35/30* (2013.01); *A61K 35/545* (2013.01)

(58) Field of Classification Search
CPC .................................................. A61K 38/57
See application file for complete search history.

(56) References Cited

U.S. PATENT DOCUMENTS

2009/0186007 A1    7/2009    Cordelier et al.

FOREIGN PATENT DOCUMENTS

| EP | 1764372 A1 * | 3/2007 | ......... A61K 38/1709 |
| KR | 10-2010-0114170 A | 10/2010 | |
| KR | 10-2015-0145891 A | 12/2015 | |
| WO | WO-2007039109 A1 * | 4/2007 | ......... A61K 38/1709 |

OTHER PUBLICATIONS

Gardner et al. "Tissue Inhibitor of Metalloproteinase (TIMP)-1: The TIMPed Balance of Matrix Metalloproteinases in the Central Nervous System", J Neurosci Res, 2003, pp. 801-806). (Year: 2003).*
Baranger et al. "Chapter 14—Endogenous and synthetic MMP inhibitor in CNS physiopathology", Progress in Brain Research, 7 pages 2014, pp. 313-351 (Year: 2014).*
Marei et al. "Potential of Stem Cell-Based Therapy for Ischemic Stroke", Frontiers in Neurology, 2018 (Year: 2018).*
E. Milia-Argeiti, et al., "Imbalance of MMP-2 and MMP-9 expression versus TIMP-1 and TIMP-2 reflects increased invasiveness of human testicular germ cell tumours", International Journal of Andrology ISSN 0105-6263, 2012, pp. 835-844, vol. 35, No. 6.
Yasuhiko Kiyozuka, et al., "Expression of Matrix Metalloproteinases and Tissue Inhibitors of Metalloproteinases in Gliomatosis Peritonei Derived from Ovarian Immature Teratoma", Acta Histochem. Cytochem., 1998, pp. 65-69, vol. 31, No. 1.
Mi-Ok Lee, et al., "Inhibition of pluripotent stem cell-derived teratoma formation by small molecules", PNAS, Aug. 5, 2013, pp. E3281-E3290.
Hitoshi Fukuda, et al., "Fluorescence-Activated Cell Sorting-Based Purification of Embryonic Stem Cell-Derived Neural Precursors Averts Tumor Formation after Transplantation", Stem Cells, 2006, pp. 763-771, vol. 24, No. 3.
Juan Liu, et al., "Suppression of Cholangiocarcinoma Cell Growth by Human Umbilical Cord Mesenchymal Stem Cells: A Possible Role of Wnt and Akt Signaling", PLOS ONE, Apr. 2013, vol. 8, Issue 4, e62844, pp. 1-11.
Lingling Hou, et al., "Inhibitory effect and mechanism of mesenchymal stem cells on liver cancer cells", Tumor Biology, pp. 1239-1250, 2014, vol. 35.
Amin Hajitou, et al., "Down-Regulation of Vascular Endothelial Growth Factor by Tissue Inhibitor of Metalloproteinase-2: Effect on in Vivo Mammary Tumor Growth and Angiogenesis1", Cancer Research, Apr. 15, 2001, pp. 3450-3457, vol. 61.
H. Li, et al., "AdTIMP-2 Inhibits Tumor Growth, Angiogenesis, and Metastasis, and Prolongs Survival in Mice", Human Gene Therapy, Mar. 20, 2001, vol. 12, pp. 515-526.
Jonathan D. Flax, et al., "Engraftable human neural stem cells respond to developmental cues, replace neurons, and express foreign genes", Nature Biotechnology, Nov. 1998, pp. 1033-1039, vol. 16.
Heon-Chang Lim, et al., "Neuroprotective effect of neural stem cell-conditioned media in in vitro model of Huntington's disease", Neuroscience Letters, 2008, pp. 175-180, vol. 435.
Office Action issued from Korean Patent Application No. 10-2018-0107637 issued on Aug. 21, 2019.
International Search Report for PCT/KR2019/008896 dated Oct. 24, 2019 (PCT/ISA/210).

* cited by examiner

*Primary Examiner* — Lianko G Garyu
(74) *Attorney, Agent, or Firm* — Sughrue Mion, PLLC

(57) ABSTRACT

The present invention relates to a composition for inhibiting teratoma formation or growth, comprising tissue inhibitor of metalloproteinase 1 (TIMP-1) or tissue inhibitor of metalloproteinase 2 (TIMP-2) as an effective component. A pharmaceutical composition for inhibiting teratoma formation or growth comprising TIMP-1 or TIMP-2 as an effective component according to the present invention, when used in stem cell therapy, can inhibit the formation and growth of teratomas caused by undifferentiated pluripotent stem cells, without affecting the differentiation potential thereof, and thus can be advantageously used as a combination drug in combination with a stem cell drug.

4 Claims, 6 Drawing Sheets

COMPOSITIONS FOR INHIBITING TERATOMA FORMATION AND GROWTH COMPRISING TIMP-1 AND TIMP-2 AS EFFECTIVE COMPONENTS

CROSS REFERENCE TO RELATED APPLICATIONS

This application is a National Stage of International Application No. PCT/KR2019/008896 filed Jul. 18, 2019, claiming priority based on Korean Patent Application No. 10-2018-0107637 filed Sep. 10, 2018, the entire disclosures of which are incorporated herein by reference.

TECHNICAL FIELD

The present invention relates to a composition for inhibiting teratoma formation or growth, the composition containing a tissue inhibitor of metalloproteinase 1 (TIMP-1) or a tissue inhibitor of metalloproteinase 2 (TIMP-2) as an active ingredient, and more particularly to a composition containing TIMP-1 or TIMP-2 capable of inhibiting the formation and growth of teratomas caused by undifferentiated pluripotent stem cells during stem cell therapy.

BACKGROUND ART

Pluripotent stem cells, that is, embryonic stem cells, are characterized by having the ability to proliferate unlimitedly through continuous self-renewal and pluripotency, that is, the ability to differentiate into all types of cells. Based on these characteristics, pluripotent stem cells may be used as cell therapy products for intractable disease treatment and regenerative medicine. However, when pluripotent stem cells remain undifferentiated without being completely differentiated during the differentiation process, they exhibit unlimited proliferative ability similar to the proliferative ability of cancer cells, and thus may form teratomas in tissues. Such teratoma formation is the greatest risk factor in clinical application of pluripotent stem cells.

In order to inhibit teratoma formation derived from pluripotent stem cells, studies have been conducted on various methods for selectively removing undifferentiated cells (Lee et al., PNAS, 110:e3281-3290, 2013), or methods of removing teratomas by sorting differentiated cells using flow cytometry (FACS) (Fukuda et al., Stem Cells 24(3): 763-771, 2006).

In recent years, it has been reported that conditioned media (CM) obtained from various types of cells can inhibit the proliferation of tumor cells (US Patent Publication No. 2009-0186007; Liu et al., PLoS One 8:e62844, 2013; Hou et al., Tumor Biology, 35:1239-50, 2014). In addition, it has been reported that activated metalloproteinase (MMP) is involved in tumor proliferation (Davidson et al., Chemistry & Industry 258-261, 1997), and that the inhibition of cancer cell proliferation and metastasis, which results from the inhibition of MMP-2/9 by TIMP, has also been reported (Hajitou et al., Cancer Res. 61:3450-3457, 2001; Li et al. Human Gene Ther. 12:515-526, 2001). However, the role of TIMP in teratomas has not yet been reported.

Accordingly, the present inventors have made extensive efforts to find a method capable of reducing the formation of teratomas caused by undifferentiated stem cells during stem cell therapy and inhibiting the growth of the teratomas, and as a result, have found that TIMP-1 or TIMP-2 is capable of inhibiting the formation and growth of teratomas by inhibiting the activity of matrix metalloproteinase 2/9 (MMP-2/9), which is expressed by pluripotent stem cells, thereby completing the present invention.

SUMMARY OF THE INVENTION

An object of the present invention is to provide a pharmaceutical composition for inhibiting teratoma formation or growth, the pharmaceutical composition containing, as an active ingredient, TIMP-1 or TIMP-2, which may be used in combination as an adjuvant for stem cell therapy by inhibiting the formation and growth of teratomas caused by undifferentiated pluripotent stem cells.

Another object of the present invention is to provide a method for producing the pharmaceutical composition, and a method of inhibiting teratoma formation or growth by administering the pharmaceutical composition.

Still another object of the present invention is to provide the use of the pharmaceutical composition either in the inhibition of teratoma formation or growth or in the manufacture of a medicament for inhibiting teratoma formation or growth.

To achieve the above objects, the present invention provides a pharmaceutical composition for inhibiting teratoma formation or growth, the pharmaceutical composition containing TIMP-1 or TIMP-2 as an active ingredient.

The present invention also provides a method for producing a composition for inhibiting teratoma formation or growth containing TIMP-1 or TIMP-2 as an active ingredient, the method comprising steps of: (a) immortalizing neural stem cells (NSCs) isolated from a brain ventricular zone; and (b) obtaining TIMP-1 or TIMP-2 in conditioned medium by culturing the immortalized neural stem cells in a non-inducing medium.

The present invention also provides a method for inhibiting teratoma formation or growth, the method comprising a step of administering a pharmaceutical composition containing TIMP-1 or TIMP-2 as an active ingredient.

The present invention also provides the use of a pharmaceutical composition containing TIMP-1 or TIMP-2 as an active ingredient in inhibition of teratoma formation or growth.

The present invention also provides the use of a pharmaceutical composition containing TIMP-1 or TIMP-2 as an active ingredient in the manufacture of a medicament for inhibition of teratoma formation or growth.

DETAILED DESCRIPTION AND PREFERRED EMBODIMENTS OF THE INVENTION

Figure 1A:
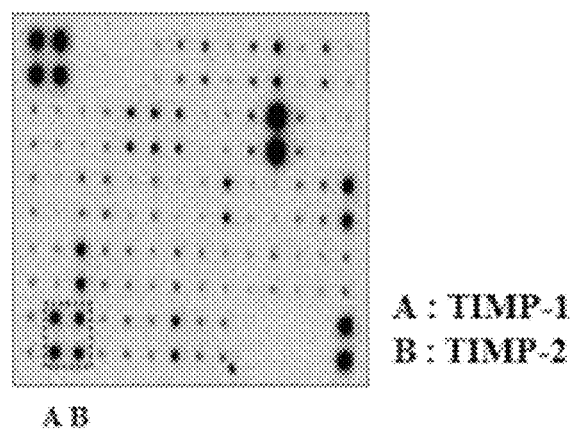
FIG. 1a shows the results of analyzing cytokines present in a neural stem cell-conditioned medium by cytokine assay.

Unless otherwise defined, all technical and scientific terms used in the present specification have the same meanings as commonly understood by those skilled in the art to which the present disclosure pertains. In general, the nomenclature used in the present specification is well known and commonly used in the art.

The greatest risk factor in stem cell therapy using pluripotent stem cells such as induced pluripotent stem cells, dedifferentiated stem cells or embryonic stem cells is the formation of teratomas (a type of cancer) caused by undifferentiated stem cells transplanted in a state of incomplete differentiation. The composition containing TIMP-1 or TIMP-2 as an active ingredient according to the present invention may inhibit the formation and growth of teratomas, and thus may greatly contribute to ensuring safety from the risk of carcinogenesis caused by residual undifferentiated stem cells. That is, when the composition containing TIMP-1 or TIMP-2 as an active ingredient according to the present invention is used in combination with embryonic stem cells or induced pluripotent stem cells in stem cell therapy, it may exhibit great synergistic effects in terms of safety and therapeutic efficacy.

In the present invention, it was confirmed that TIMP-1/2 contained in conditioned medium of neural stem cells (NSCs) inhibited the proliferation of mouse embryonic stem cells and dedifferentiated stem cells, and that this inhibition of proliferation resulted from the inhibition of MMP-2/9 activity by TIMP-1/2. In addition, it was confirmed that, when mice transplanted with embryonic stem cells were treated with TIMP-1/2 of neural stem cell-conditioned medium, the differentiation ability of the embryonic stem cells was not affected while formation and growth of teratomas were inhibited.

Therefore, in one aspect, the present invention is directed to a pharmaceutical composition for inhibiting teratoma formation or growth, the pharmaceutical composition containing TIMP-1 or TIMP-2 as an active ingredient.

In the present invention, the composition may be used in combination with a stem cell therapy product.

As used herein, the term "cell therapy product" refers to cells and tissue which are obtained by isolation from humans, culture, and special manipulation, and are used for the purposes of treatment, diagnosis and prevention. Specifically, the term refers to pharmaceutical products used for the purposes of treatment, diagnosis and prevention through a series of actions, such as proliferating or selecting allogeneic or xenogeneic cells in vitro to restore the function of cells or tissues or changing the biological properties of cells. Cell therapy products are broadly classified, according to the degree of differentiation of cells, into somatic cell therapy products and stem cell therapy products, and the present invention particularly relates to stem cell therapy products.

In the present invention, the stem cells are preferably embryonic stem cells, induced pluripotent stem cells, or adult stem cells. The adult stem cells are preferably umbilical cord blood-derived mesenchymal stem cells, bone marrow-derived mesenchymal stem cells, adipose-derived mesenchymal stem cells, muscle-derived mesenchymal stem cells, nerve-derived mesenchymal stem cells, skin-derived mesenchymal stem cells, amniotic membrane-derived skin-derived mesenchymal stem cells stem cells, and placenta-derived mesenchymal stem cells, but are not limited thereto.

As used herein, the term "embryonic stem cell" refers to pluripotent cells obtained by culturing cells isolated from the inner cell mass of a blastocyst in the initial stage of development after fertilization. As used herein, the term "pluripotent stem cell" refers to pluripotent cells capable of differentiating into all three germ layers constituting a living body, that is, the endoderm, the mesoderm, and the ectoderm.

The term "adult stem cell" as used herein refers to multipotent and unipotent stem cells that may be obtained from skin, blood vessels, muscles and brain. Representative adult stem cells include mesenchymal stem cells (MSCs) and hematopoietic stem cells (HSCs). Mesenchymal stem cells are known to differentiate into chondrocytes, osteoblasts, adipocytes, myocytes, and neurons, and it is known that hematopoietic stem cells differentiate mainly into blood cells such as red blood cells, white blood cells, and platelets.

The term "mesenchymal stem cell" as used herein refers to undifferentiated stem cells isolated from human or mammalian tissues, which may be derived from various tissues. In particular, mesenchymal stem cells include umbilical cord-derived mesenchymal stem cells, umbilical cord blood-derived mesenchymal stem cells, bone marrow-derived mesenchymal stem cells, adipose-derived mesenchymal stem cells, muscle-derived mesenchymal stem cells, nerve-derived mesenchymal stem cells, skin-derived mesenchymal stem cells, amniotic membrane-derived mesenchymal stem cells, and placenta-derived mesenchymal stem cells, and technology for isolating stem cells from each tissue is already known in the art.

The term "differentiation" as used herein refers to a phenomenon in which the structure or function of cells is specialized during the division, proliferation and growth of cells, that is, a phenomenon in which cells, tissues, etc. of an organism change their shape or function in order to perform their own task.

As used herein, the term "used in combination", "combination therapy" or "co-administration" refers to a method of administering individual therapeutic components simultaneously, sequentially, or individually. Specifically, the term means obtaining the effect of combination therapy by a method of administering two or more drugs simultaneously or sequentially, or by a method of alternately administering two or more drugs at regular or random intervals. The combination therapy is defined as a method whose therapeutic effect measured based on the degree of response, the rate of response, the period until disease progression, or the survival period is better than the effect obtainable by administering each of the components for combination therapy alone at a conventional dose, and which may provide a synergistic effect.

In the present invention, the TIMP-1 or TIMP-2 may be derived from neural stem cells.

In the present invention, the neural stem cells are not limited as to the type thereof. Preferably, they are fetus-derived adult stem cells. In a specific example of the present invention, neural stem cells extracted from a ventricular zone of the fetal brain were used, but the present invention is not limited thereto.

As used herein, the term "neural stem cell-conditioned medium" means a medium containing components released from cells obtained during subculture of neural stem cells that are a kind of ectodermal stem cells.

Figure 1B:
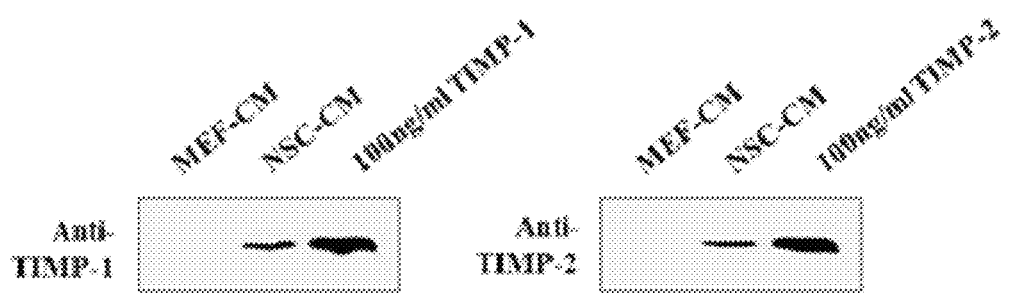
FIG. 1b shows the results of confirming TIMP 1/2 present in neural stem cell-conditioned medium by Western blot assay.

In a specific example of the present invention, in order to confirm that the composition containing, as an active ingredient, TIMP 1/2 in neural stem cell-conditioned medium, inhibits teratoma formation and growth, the supernatant obtained from the neural stem cell-conditioned medium was analyzed by cytokine array (FIGS. 1a and 1b). The neural stem cell-conditioned medium of the present invention contains TIMP 1/2, as confirmed by Western blot analysis (FIG. 1).

Figure 2A:
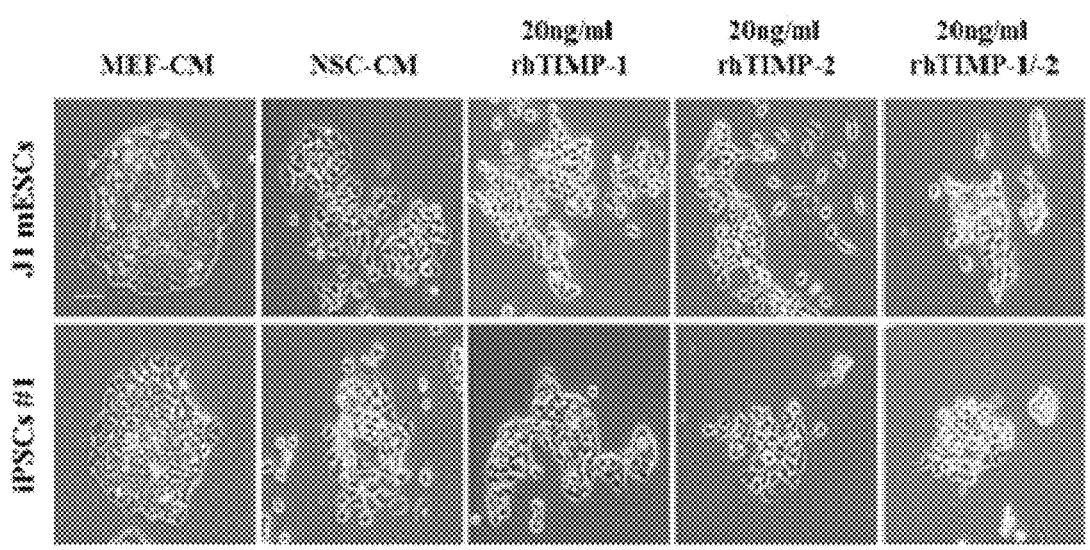
FIGS. 2a and 2b shows the results of confirming the inhibition of proliferation of mouse embryonic stem cells treated with each or a combination of a neural stem cell-conditioned medium or the recombinant protein TIMP 1/2.
Figure 2B:
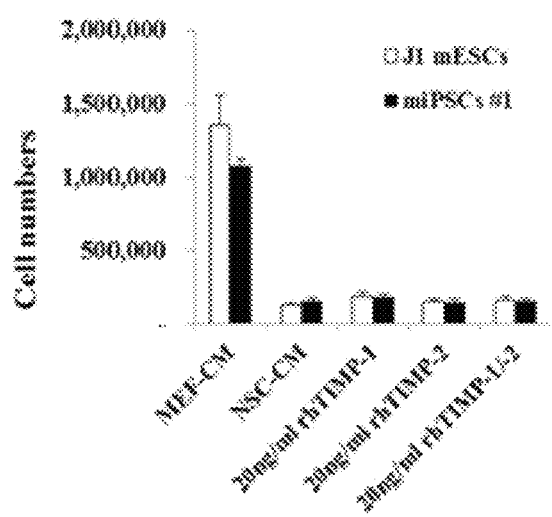
Figure 3A:
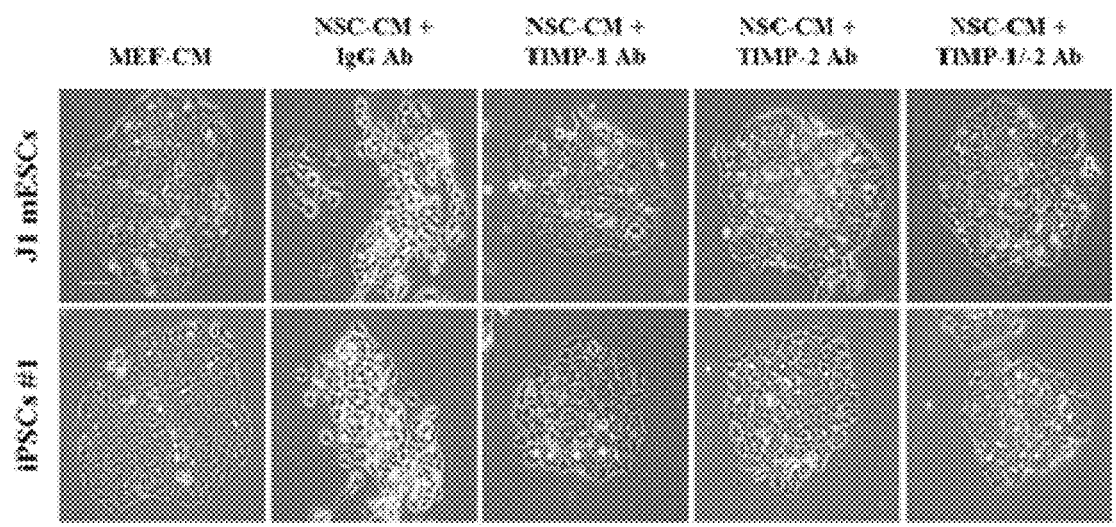
FIGS. 3a and 3b shows the results of confirming the inhibition of proliferation of mouse dedifferentiated stem cells treated with each or a combination of a neural stem cell-conditioned medium or the recombinant protein TIMP 1/2.
Figure 3B:
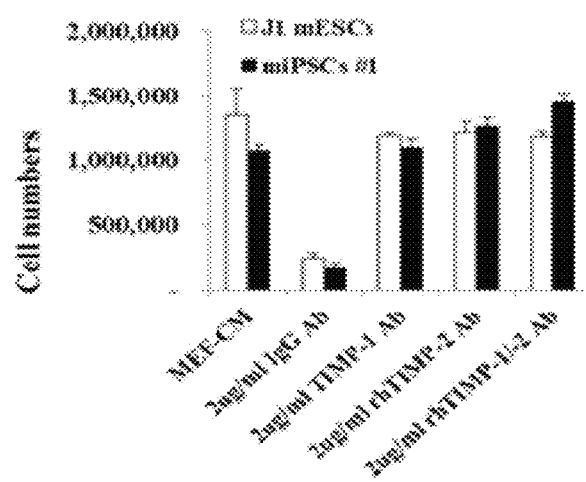

In a specific example of the present invention, it was confirmed that the growth of mouse embryonic stem cells was inhibited by treatment with each or a combination of the neural stem cell-conditioned medium and the recombinant protein TIMP 1 or TIMP 2 (FIGS. 2a and 2b). In addition, it was confirmed that the growth of mouse dedifferentiated stem cells was also inhibited by treatment with each or a combination of the neural stem cell-conditioned medium and the recombinant protein TIMP 1 or TIMP 2 (FIGS. 3a and 3b).

Figure 4:
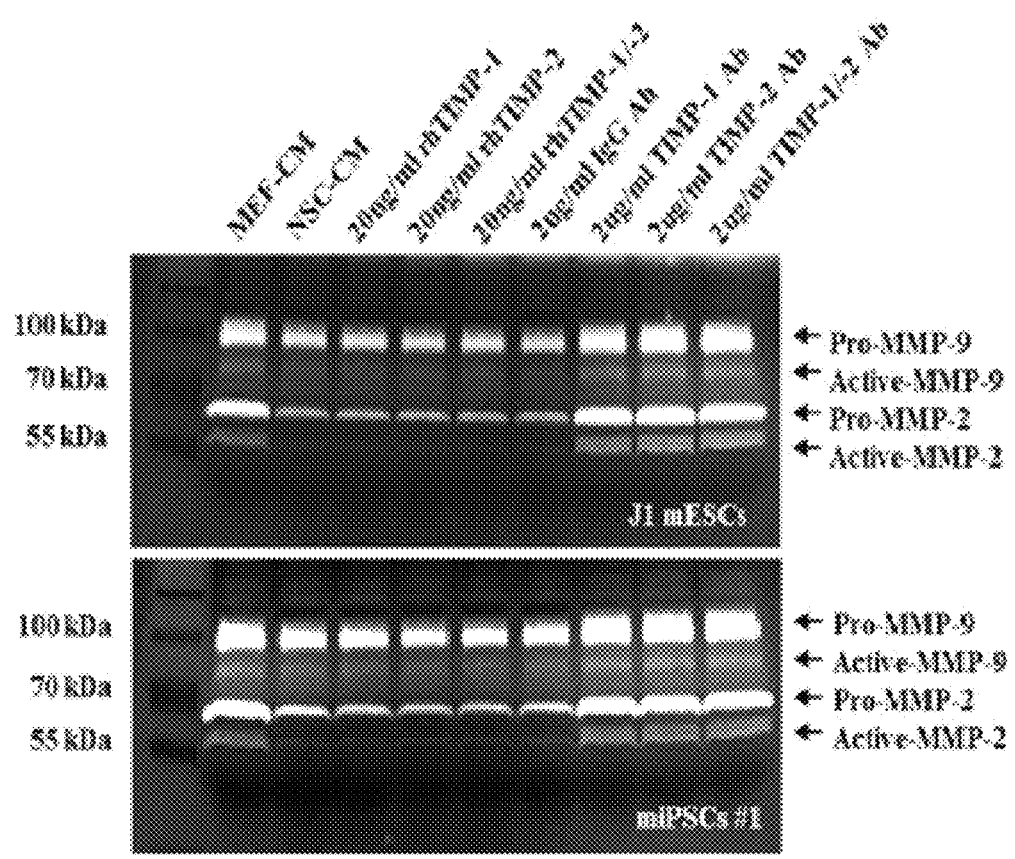
FIG. 4 shows the results of confirming the inhibition of MMP-2/9 activity in medium treating mouse embryonic stem cells and dedifferentiated stem cells with each or a combination of a neural stem cell-conditioned medium or the recombinant protein TIMP 1/2.

It was confirmed that, when mouse embryonic stem cells and dedifferentiated stem cells were treated with each or a combination of the neural stem cell-conditioned medium and the recombinant protein TIMP 1 or TIMP 2, followed by blocking with an antibody, the activity of MMP-2/9 expressed in the cells was inhibited by TIMP 1 or TIMP 2 (FIG. 4).

Figure 5:
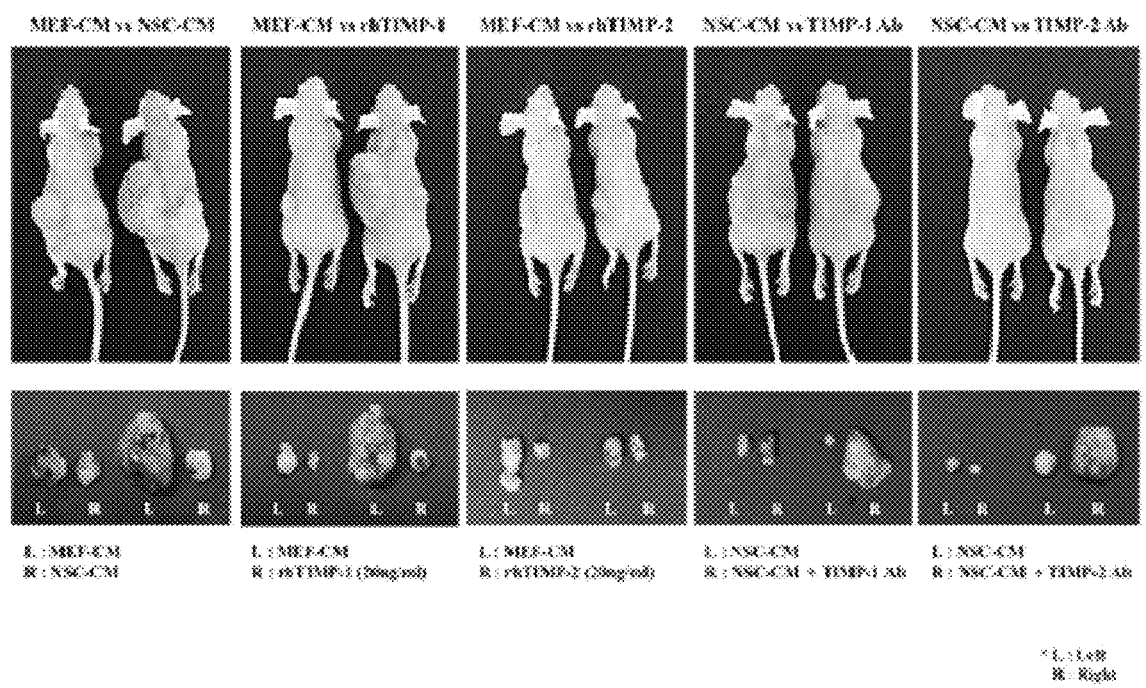
FIG. 5 shows the results of confirming the inhibition of teratoma formation and growth after transplanting mouse embryonic stem cells into immunodeficient nude mice and treating the nude mice with each or a combination of a neural stem cell-conditioned medium or the recombinant protein TIMP 1/2.
Figure 6:
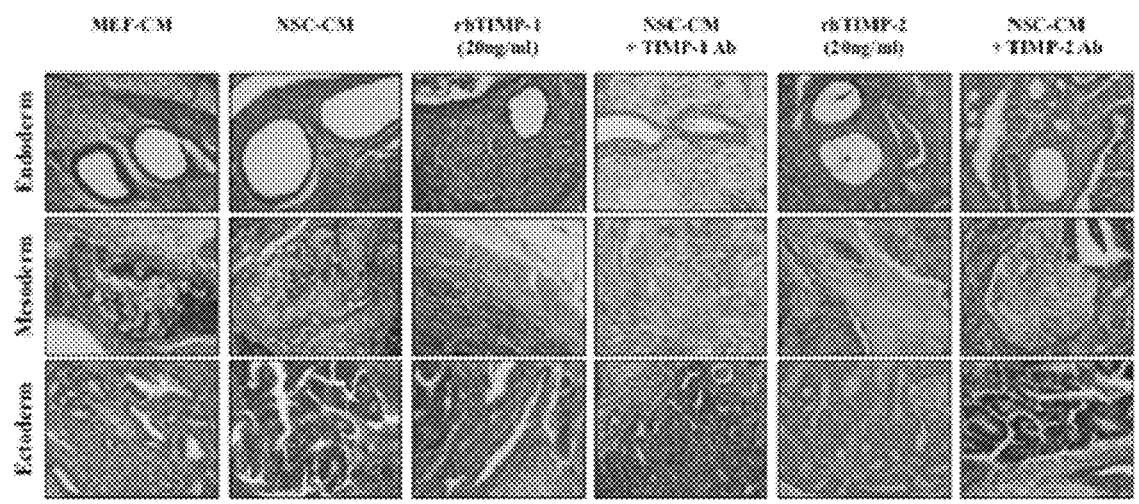
FIG. 6 shows the results of confirming that there was no change in differentiation ability when teratoma formation and teratoma growth were inhibited, after transplanting mouse embryonic stem cells into immunodeficient nude mice and treating the nude mice with each or a combination of a neural stem cell-conditioned medium or the recombinant protein TIMP 1/2.

Finally, in a specific example of the present invention, it was confirmed that, when mice transplanted with mouse embryonic stem cells were treated with each or a combination of the neural stem cell-conditioned medium and the recombinant protein TIMP 1 or TIMP 2, followed by blocking with an antibody, teratoma formation and growth in the mice were inhibited (FIG. 5). In addition, it was confirmed that, when mice transplanted with mouse embryonic stem cells were treated with each or a combination of the neural stem cell-conditioned medium and the recombinant protein TIMP 1 or TIMP 2, followed by blocking with an antibody, the normal differentiation capacity of the cells did not change, even though teratoma formation and growth were inhibited (FIG. 6).

For use, the pharmaceutical composition of the present invention may be formulated into oral preparations, such as powders, granules, capsules, tablets, aqueous suspensions, emulsion, syrups and aerosol as well as external preparations, suppositories, and sterile injectable solutions, according to the respective conventional methods. Carriers, excipients and diluents that may be contained in the composition containing TIMP 1 or TIMP 2 include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil.

The composition of the present invention is formulated with commonly used diluents or excipients, such as fillers, extenders, binders, wetting agents, disintegrants, and surfactants. Solid formulations for oral administration include tablets, pills, powders, granules, capsules and the like, and such solid formulations are prepared by mixing the composition with one or more excipients, for example, starch, calcium carbonate, sucrose, lactose or gelatin. In addition to simple excipients, lubricants such as magnesium stearate or talc may also be used. Liquid formulations for oral administration include suspensions, solutions, emulsions, and syrups, and may contain various excipients, for example, wetting agents, flavoring agents, aromatics and preservatives, in addition to water and liquid paraffin, which are frequently used simple diluents. Formulations for parenteral administration include sterile aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, and the like may be used. As bases for suppositories, Witepsol, Macrogol, Tween 60, cacao butter, laurin fat, glycerogelatin and the like may be used. In addition, a filler, an anti-aggregating agent, a lubricant, a wetting agent, a fragrance emulsifier, a preservative, etc. may be additionally included.

In another aspect, the present invention is directed to a method for producing a composition for inhibiting teratoma formation or growth containing TIMP-1 or TIMP-2 as an active ingredient, the method comprising steps of: (a) immortalizing neural stem cells (NSCs) isolated from a brain ventricular zone; and (b) obtaining TIMP-1 or TIMP-2 in conditioned medium by culturing the immortalized neural stem cells in non-inducing medium.

In the present invention, the composition may be used in combination with a stem cell therapy product.

In the present invention, the stem cells are preferably embryonic stem cells or induced pluripotent stem cells, without being limited thereto.

As the medium for culturing neural stem cells in the present invention, a basal medium known in the art may be used without limitation. The basal medium may be artificially produced by synthesis, or a commercially produced medium may also be used. Examples of the commercially produced medium include, but are not limited to, DMEM (Dulbecco's Modified Eagle's Medium), MEM (Minimal Essential Medium), BME (Basal Medium Eagle), RPMI 1640, F-10, F-12, α-MEM (α-Minimal Essential Medium), G-MEM (Glasgow's Minimal Essential Medium), and Isocove's Modified Dulbecco's Medium. The commercially produced medium may be DMEM.

In addition, the basal medium preferably contains 5 to 10% (v/v) FBS, and in a specific example of the present invention, neural stem cells were cultured in DMEM.

The present invention provides a method for producing the composition, the method comprising steps of: culturing neural stem cells; and isolating the neural stem cells from the culture medium. The production of the composition may be performed by any method that is commonly used, and the process of isolating, culturing, and isolating the neural stem cells is not limited to the method of the present invention and may be performed by any conventional method known in the art.

Preferably, the neural stem cells are cells obtained by immortalizing neural stem cells extracted from the brain ventricular zone. In a specific example of the present invention, adult neural stem cells (NSCs) isolated from the ventricular zone of the fetal brain were immortalized to obtain cells for use in the present invention. Then, the immortalized cells were cultured in a non-inducing medium containing DMEM (Dulbecco's Modified Eagle's Medium), 10% FBS (fetal bovine serum) and 1% penicillin streptomycin, and non-adherent cells were removed. In the process of subculturing the neural stem cells (NSCs) cultured as described above, the conditioned medium was collected. The collected medium was centrifuged, and the supernatant was collected by filtration.

In the present invention, the non-inducing medium preferably contains DMEM (Dulbecco's Modified Eagle's Medium), 10% FBS (fetal bovine serum) and 1% penicillin/streptomycin, but is not limited thereto.

As described above, TIMP-1 or TIMP-2 contained in the ectoderm-derived neural stem cell conditioned medium according to the present invention may be advantageously used as a raw material for the development of a drug (quasi-drug) product that inhibits teratoma formation and growth.

In still another aspect, the present invention is directed to the use of a pharmaceutical composition containing TIMP-1 or TIMP-2 as an active ingredient in inhibition of teratoma formation or growth.

In yet another aspect, the present invention is directed to the use of a pharmaceutical composition containing TIMP-1 or TIMP-2 as an active ingredient in the manufacture of a medicament for inhibition of teratoma formation or growth.

In still yet another aspect, the present invention is directed to a method for inhibiting teratoma formation or growth, the method comprising a step of administering a pharmaceutical composition containing TIMP-1 or TIMP-2 as an active ingredient.

As used herein, the term "administration" means providing a given substance to a patient by any suitable method. The composition of the present invention may be administered by any general route, as long as it may reach a target tissue.

The composition of the present invention may be administered through various routes such as oral, intravenous, subcutaneous, intradermal, intranasal, intraperitoneal, intramuscular, and transdermal routes. The dose of the composition of the present invention may vary depending on the patient's age, sex and body weight, and may be easily determined by those skilled in the art. Preferably, the composition of the present invention may be administered orally or parenterally. In addition, the dose of the composition may be determined by those skilled in the art depending on various related factors, including the route of administration, the severity of the disease, and the patient's sex, body weight and age, as well as the type of drug which is an active ingredient, and thus the dose is not intended to limit the scope of the present invention in any way.

EXAMPLES

Hereinafter, the present invention will be described in more detail with reference to examples. It will be obvious to those skilled in the art that these examples serve merely to illustrate the present invention, and the scope of the present invention is not limited by these examples.

Example 1: Production of Neural Stem Cell-Conditioned Medium

Cells were obtained by immortalizing adult neural stem cells (NSCs) isolated from the ventricular zone of the fetal brain. Specifically, 14-week-old fetal neural cell tissue was dissociated into single cells by treatment with a solution containing 0.1% collagenase and 0.1% hyaluronidase at 37° C. for 1 hour and treatment with 0.05% Trypsin-EDTA for 2 to 3 minutes. Then, the cells were isolated by FACS using markers (CD45−/CD133+/CD34−). The isolated cells were cultured in human neurosphere culture media containing N-2 supplements, 0.2 mg/ml heparin, 20 ng/ml bFGF (basic Fibroblast Growth Factors), 20 ng/ml EGF (Epidermal Growth Factor) and 10 ng/ml LIF (leukemia inhibitory factor). After 10 to 14 days, the formed neurospheres were separated into single cells by treatment with collagenase, and the v-myc gene was transduced into the cells using a retroviral vector. The cells obtained in the selection process were cultured in a non-inducing medium containing DMEM (Dulbecco's Modified Eagle Medium), 10% FBS (fetal bovine serum) and 1% penicillin/streptomycin (Flax J D et al., *Nature Biotechnology*, vol. 16, 1998; Lim H-C et al., *Neuroscience Letters* 435:175-180, 2008).

The cells were dispensed into a 150 mm culture dish at a density of $5 \times 10^5$ cells and 15 ml of culture medium was added thereto, and then the culture medium was collected at a confluence of 80% in an incubator at 37° C. under 5% $CO_2$. At this time, the culture medium was a non-inducing medium containing DMEM, 10% FBS and 1% penicillin/streptomycin, and after culturing, non-adherent cells were removed. The neural stem cells (NSCs) cultured through the above-described process were subcultured, and the conditioned medium was collected.

Example 2: Cytokine Assay of Neural Stem Cell-Conditioned Medium

For cytokine assay, the neural stem cell-conditioned medium produced by the method of Example 1 was incubated in a serum-free condition for 48 hours, and then the conditioned medium was collected. A sample was prepared so that the amount of protein in the conditioned medium was 200 μg, and then the sample was analyzed by cytokine array (FIG. 1a).

In addition, as a result of further analyzing TIMP 1/2 in the neural stem cell-conditioned medium by Western blot analysis, as shown in FIG. 1b, it was confirmed that TIMP 1/2 was present in the neural stem cell-conditioned medium.

Example 3: Confirmation of Inhibition of Mouse Embryonic Stem Cell Growth by Treatment with Neural Stem Cell-Conditioned Medium $1 \times 10^5$ mouse embryonic stem cells were dispensed into a 60-mm culture dish. The next day, the cells were treated with each or a combination of the neural stem cell-conditioned medium and the recombinant protein TIMP 1/2 for 72 hours. Next, the cells were detached, and proliferation of the cells was evaluated by doubling time.

As a result, it was confirmed that proliferation of the mouse embryonic stem cells was inhibited due to TIMP 1/2 in the neural stem cell-conditioned medium (FIGS. 2a and 2b).

Example 4: Confirmation of Inhibition of Mouse Dedifferentiated Stem Cell Growth by Treatment with Neural Stem Cell-Conditioned Medium $1 \times 10^5$ mouse dedifferentiated stem cells were dispensed into a 60-mm culture dish. The next day, the cells were treated with each or a combination of the neural stem cell-conditioned medium and the recombinant protein TIMP 1/2 for 72 hours. Next, the cells were detached, and proliferation of the cells was evaluated by doubling time.

As a result, it was confirmed that proliferation of the mouse dedifferentiated stem cells was inhibited due to TIMP 1/2 in the neural stem cell-conditioned medium (FIGS. 3a and 3b).

Example 5: Inhibition of MMP-2/9 Activity in Mouse Embryonic Stem Cells and Dedifferentiated Stem Cells by Treatment with Neural Stem Cell-Conditioned Medium $1 \times 10^5$ mouse embryonic stem cells or mouse dedifferentiated stem cells were dispensed into a 60-mm culture dish. The next day, the cells were treated with each or a combination of the neural stem cell-conditioned medium and the recombinant protein TIMP 1/2 for 72 hours, and then the conditioned medium was collected. The activity of MMP-2/9 in the collected conditioned medium was measured by gelatin zymogram.

As a result, it was confirmed that activity of MMP-2/9 was inhibited TIMP 1/2 in the neural stem cell-conditioned medium (FIG. 4).

Example 6: Confirmation of Teratoma Formation and Growth by Treatment with Neural Stem Cell-Conditioned Medium Six-week-old Balb/c-nu female mice were acclimated for one week, and then transplanted subcutaneously with $5 \times 10^5$ embryonic stem cells through Matrigel to form teratomas. The next day, each of the neural stem cell-conditioned medium and the recombinant protein TIMP 1/2 was injected subcutaneously into the site of embryonic stem cell transplantation through an insulin syringe once a day for 21 days. After 21 days, teratomas were isolated from the mice.

As a result, it was confirmed that teratoma formation and growth in the immunodeficient nude mice transplanted with the embryonic stem cells were inhibited due to TIMP 1/2 in the neural stem cell-conditioned medium (FIG. 5).

Example 7: Evaluation of Differentiation Ability Upon Inhibition of Teratoma Formation and Growth by Treatment with Neural Stem Cell-Conditioned Medium Differentiation ability in the teratomas isolated in Example 6 was evaluated. Specifically, 21 days after transplantation of the embryonic stem cells into the mice, teratomas were isolated and fixed in 4% formaldehyde, and the tissue embedded in paraffin was sectioned to a thickness of 3 μm and attached to slides, followed by deparaffinization and rehydration. Next, three germ layers (ectoderm, mesoderm and endoderm) in the growth-inhibited teratomas were analyzed by hematoxylin and eosin (H&E) staining.

As a result, it was confirmed that, even when teratoma formation and growth were inhibited due to TIMP 1/2 in the neural stem cell-conditioned medium, the three germ layers were normally formed, suggesting that differentiation ability did not change (FIG. 6).

INDUSTRIAL APPLICABILITY

The pharmaceutical composition for inhibiting teratoma formation or growth containing TIMP-1 or TIMP-2 as an active ingredient according to the present invention inhibits the formation and growth of teratomas caused by undifferentiated pluripotent stem cells without affecting differentiation ability, and thus may be effectively used as a co-therapeutic agent for stem cell therapy, which may exhibit a synergistic effect when used in combination with a stem cell therapy product.

Although the present invention has been described in detail with reference to specific features, it will be apparent to those skilled in the art that this detailed description is only of a preferred embodiment thereof, and does not limit the scope of the present invention. Thus, the substantial scope of the present invention will be defined by the appended claims and equivalents thereto.

The invention claimed is:

1. A method for inhibiting teratoma formation or growth comprising administering a composition comprising TIMP-1 or TIMP-2 as an active ingredient to a subject in need thereof,
   wherein the composition is produced by a process comprising steps of:
   (a) immortalizing neural stem cells (NSCs) isolated from a brain ventricular zone; and
   (b) obtaining TIMP-1 or TIMP-2 in conditioned medium by culturing the immortalized neural stem cells in a non-inducing medium.

2. The method of claim 1, the composition is used in combination with stem cells.

3. The method of claim 2, wherein the stem cells are embryonic stem cells, induced pluripotent stem cells, or adult stem cells.

4. The method of claim 1, wherein the non-inducing medium comprises DMEM (Dulbecco's Modified Eagle's Medium), 10% FBS (fetal bovine serum) and 1% penicillin/streptomycin.

* * * * *